United States Patent [19]
Collins et al.

[11] 3,970,683
[45] July 20, 1976

[54] 11,15-DIHYDROXY-9-OXOPROST-13-YNOIC ACID

[75] Inventors: Paul W. Collins, Wheeling; Raphael Pappo, Skokie, both of Ill.

[73] Assignee: G. D. Searle & Co., Chicago, Ill.

[22] Filed: Nov. 12, 1974

[21] Appl. No.: 523,169

Related U.S. Application Data

[60] Division of Ser. No. 244,238, April 14, 1972, abandoned, which is a continuation-in-part of Ser. No. 223,299, Feb. 3, 1972.

[52] U.S. Cl. .................. 260/468 D; 260/240 R; 260/345.1; 260/345.7; 260/345.8; 260/345.9; 260/429 R; 260/438.1; 260/448 R; 260/448.8 R; 260/468 R; 260/488 R; 260/488 H; 260/514 D; 260/514 R; 260/606.5 B; 424/305; 424/317
[51] Int. Cl.² .................. C07L 61/38; C07L 69/74
[58] Field of Search .................. 260/468 D, 514 D

[56] References Cited
OTHER PUBLICATIONS
Pappo et al., Prostaglandins, Annals of N.Y. Acad. of Sci. 180, 64 (1971).

Primary Examiner—Robert Gerstl
Attorney, Agent, or Firm—John A. Dhuey

[57] ABSTRACT

3-(Optionally oxygenated)-5-oxocyclopent-1-enealkanoic acids and their alkyl esters are allowed to react with appropriate alkenyl copper, alkenyl boron, alkynyl boron, alkynyl gallium or alkynyl aluminum compounds to produce the corresponding 2-(3-hydroxy-3-[optionally alkylated]-1-alkenyl)cyclopentanealkanoic acids, 2-(3-hydroxy-3-[optionally alkylated]-1-alkynyl)cyclopentanealkanoic acids and their esters. The prostaglandin derivatives so produced are valuable and useful as pharmacological agents as is evidenced by their central nervous system-affective, anti-bacterial, anti-fungal and prostaglandin antagonist activity.

9 Claims, No Drawings

11,15-DIHYDROXY-9-OXOPROST-13-YNOIC ACID

This application is a division of our copending application Ser. No. 244,238, filed Apr. 14, 1972, now abandoned, which is a continuation-in-part of our copending application entitled "15-Desoxy and 11,15-Bisdesoxy Prostaglandin Derivatives," Ser. No. 223,299, filed Feb. 3, 1972.

The present invention is concerned generally with prostaglandins, prostaglandin derivatives and the process of their manufacture. In particular, it is concerned with a process for the production of $PGE_1$ and its derivatives of the following structural formula

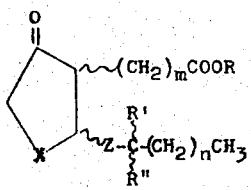

wherein X is a methylene, hydroxymethylene, tetrahydropyranyloxymethylene, (lower alkoxyalkyl)oxymethylene, tri(lower alkyl)siloxymethylene, or (lower alkanoyl)oxymethylene radical, R is hydrogen or a lower alkyl radical containing 1 to 7 carbon atoms, R' is hydrogen or a lower alkyl radical containing 1–4 carbon atoms, R'' is hydrogen or a hydroxy, tetrahydropyranyloxy, lower alkoxyalkyloxy or tri(lower alkyl)siloxy radical, Z is a vinylene or ethynylene radical, m is an integer greater than 5 and less than 8, n is an integer greater than 1 and less than 9 and the wavy line represents the alternative α or β configuration or the epimeric mixture.

The lower alkanoyl radicals represented for the purposes of this invention contain 1 to 7 carbon atoms and are illustrated by formyl, acetyl and propionyl and the lower alkyl radicals contain 1 to 7 carbon atoms and are illustrated by methyl, ethyl, propyl and isopropyl.

The lower alkoxyalkyl radicals consist of lower alkoxy radicals containing 1 to 7 carbon atoms and lower alkyl radicals containing 1 to 7 carbon atoms. They are illustrated by methoxymethyl, ethoxyethyl, isopropoxymethyl and the like A preferred embodiment of the process of this invention utilizes as starting materials compounds of the following structural formula

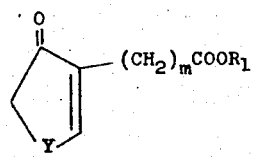

wherein m is as defined hereinbefore, Y is a methylene, hydroxymethylene, (lower alkanoyl)oxymethylene, (lower alkoxy)alkyloxymethylene, tri(lower alkyl)siloxymethylene or tetrahydropyranyloxymethylene radical and $R_1$ is hydrogen, a lower alkyl radical or a tetrahydropyranyl radical. Those compounds are prepared by methods described by Bagli et al., *Tetrahedron Letters*, 465 (1966) and Heslinga et al., *Rec. Trav. Chim.*, 87, 1421 (1968).

The instant process is practiced by contacting the above described compounds with an appropriate alkenyl copper, alkenyl boron, alkynyl boron, alkynyl gallium or alkynyl aluminum compound selected from the group described by the following structural formulas

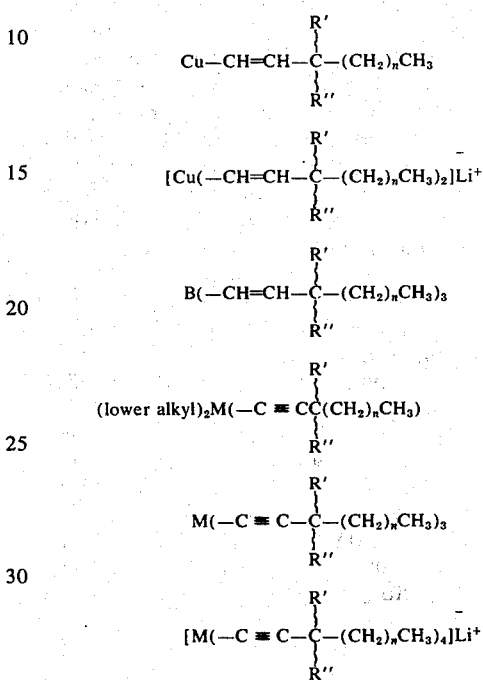

wherein R', R'' and n are the same as previously defined and M is aluminum, gallium or boron.

The trans-1-alkenyl copper compounds represented above are prepared by the addition of cuprous iodide to the appropriate trans-1-alkenyl magnesium chloride in a suitable solvent such as tetrahydrofuran. The trans-1-alkenyl magnesium chlorides are prepared by contacting magnesium, activated with mercuric chloride, with trans-1-alkenyl mercuric chloride which is produced by first contacting the 1-alkynes with catechol borane and then treating that product with mercuric chloride.

Alternatively, the trans-1-alkenyl copper derivatives can be prepared by contacting the trans-1-alkenyl mercuric chlorides with lithium metal, thus yielding the trans-1-alkenyl lithium compounds which are treated with cuprous iodide to form the desired trans-1-alkenyl copper derivatives.

The cis-1-alkenyl copper reactants are prepared from the cis-1-alkenyl bromides by successive treatment with lithium or magnesium and cuprous iodide. The method of preparation of the cis-1-alkenyl bromides is described by G. B. Bachman, *J.A.C.S.*, 55, 4279 (1933).

Formation of the trialkynyl aluminum and gallium compounds is accomplished by treating the appropriate 1-alkyne with butyl lithium and then with aluminum trichloride and gallium trichloride, respectively. The trialkynyl boron compounds are formed in the same manner except that boron trichloride, boron tribromide, boron trifluoride or boron trifluoride etherate is employed. The reactions are generally carried out in a suitable solvent such as ethyl ether, tetrahydrofuran or toluene.

Typically, trans-1-hexenyl mercuric chloride is produced by contacting 1-hexyne with catechol borane and then with mercuric chloride. The trans-1-hexenyl mercuric chloride then is added to a suspension of magnesium powder and tetrahydrofuran. The trans-1-hexenyl magnesium chloride which results is not isolated but is treated with cuprous iodide to form the immediate reactant, trans-1-hexenyl copper, which is employed in situ and treated with tetrahydropyran-2-yl 5-oxocyclopent-1-eneheptanoate to produce the instant 2-(1-hexenyl)-5-oxocyclopentaneheptanoic acid.

The preparation of the 2-alkynyl-cyclopentanealkanoic acid derivatives is illustrated by the treatment of 1-octyne with butyl lithium followed by the addition of aluminum trichloride to produce trioctynyl aluminum which is employed in situ and allowed to react with methyl 3-hydroxy-5-oxocyclopent-1-eneheptanoate, thus producing the instant methyl 3-hydroxy-2-(1-octynyl)-5-oxocyclopentaneheptanoate The 2-(3-hydroxy-3-[optionally alkyl]-1-alkynyl) derivatives are produced in the same manner as the desoxy compounds except that the 3-tetrahydropyranyl, 3-lower alkoxyalkyl or 3-tri(lower alkyl)silyl ethers of the substituted metallic alkynyl reactants are employed. The ether function is subsequently hydrolyzed to the hydroxyl moiety to obtain the desired products.

Thus, treatment of methyl 3(RS)-hydroxy-5-oxocyclopent-1-eneheptanoate with tri(3(RS)-[tetrahydropyran-2-yl]oxy-1-octynyl) aluminum followed by hydrolysis of the ether moiety with aqueous acetic acid in tetrahydrofuran affords the instant methyl 3(R)-hydroxy-2α-(3(R)-hydroxy-1-octynyl)-5-oxocyclopentane-1β-heptanoate, methyl 3(R)-hydroxy-2α-(3(S)-hydroxy-1-octynyl)-5-oxocyclopentane-1β-heptanoate, methyl 3(R)-hydroxy-2α-(3(R)-hydroxy-1-octynyl)-5-oxocyclopentane-1α-heptanoate, methyl 3(R)-hydroxy-2α-(3(S)-hydroxy-1-octynyl)-5-oxocyclopentane-1α-heptanoate and their enantiomers as racemic mixtures.

Contacting methyl 3(RS)-hydroxy-5-oxocyclopent-1-eneheptanoate with the boron reactant in place of the aluminum reactant affords the same compounds described above and, in addition, also effords methyl 3(R)-hydroxy-2β-(3(R)-hydroxy-1-octynyl)-5-oxocyclopentane-1α-heptanoate, methyl 3(R)-hydroxy-2β-(3(S)-hydroxy-1-octynyl)-5-oxocyclopentane-1α-heptanoate, methyl 3(R)-hydroxy-2β-(3(R)-hydroxy-1-octynyl)-5-oxocyclopentane-1β-heptanoate, methyl 3(R)-hydroxy-2β-(3(S)-hydroxy-1-octynyl)-5-oxocyclopentane-1β-heptanoate and their enantiomers as racemic mixtures. The 3(R),2β,1β-compounds can be isomerized to the 3(R),2β,1α-compounds by treatment with potassium acetate under refluxing conditions.

Preparation of the 3-(tetrahydropyran-2-yl)oxy-trans-1-alkenyl copper compounds begins with the treatment of the 1-alkyn-3-ols with dihydropyran to afford the 3-tetrahydropyranyl ethers. The ethers are contacted with diisobutyl aluminum hydride and then iodine or bromine to afford the trans-1-halogenated-1-alken-3-ol 3-tetrahydropyran-2-yl ethers. Further treatment with magnesium metal, activated with mercuric chloride, followed by treatment with cuprous iodide affords the desired 3-(tetrahydropyran-2-yl)oxy-trans-1-alkenyl copper reactants.

Typically, 1-octyn-3-ol is allowed to react with dihydropyran in the presence of a catalytic amount of p-toluenesulfonic acid to form the 3-pyranyl ether. 3-(tetrahydropyran-2-yl)oxy-1-octyne. That material is treated with diisobutyl aluminum hydride, then with iodine, to yield the corresponding iodo-octene, 3-(tetrahydropyran-2-yl)oxy-1-iodo-1-octene. Magnesium metal, activated with mercuric chloride, is added to the iodo-octene and that addition is followed by the addition of cuprous iodide to yield 3-(tetrahydropyran-2-yl)oxy-trans-1-octenyl copper.

Alternatively, the 3-(tetrahydropyran-2-yl)oxy-trans-1-alkenyl copper compounds may be prepared by first reducing the 1-alkyn-3-ols with lithium aluminum hydride to form the 1-alken-3-ols. Treatment of those compounds with dihydropyran followed by halogenation with bromine or iodine in chloroform yields the corresponding 3-(tetrahydropyran-2-yl)oxy-1,2-dihalogenated-alkanes. Dehydrohalogenation with potassium t-butoxide in t-butanol or with 1,5-diazabicyclo[4.3.0]non-5-ene in dimethyl sulfoxide affords the 1-halogenated-3-(tetrahydropyran-2-yl)oxy-trans-1-alkenes, which are treated with magnesium metal activated with mercuric chloride, and then with cuprous iodide to obtain the 3-(tetrahydropyran-2-yl)oxy-trans-1-alkenyl copper compounds. Thus, when 1-octyne-3-ol is allowed to react according to the above sequence of reactions, there is obtained 3-(tetrahydropyran-2-yl)oxy-trans-1-octenyl copper.

The cis-1-alkenyl copper reactants are prepared by reducing the 1-alkyne-3-ols with a reducing agent such as lithium aluminum hydride and then halogenating with iodine or bromine and distilling under reduced pressure to yield the cis-1-halogenated-1-alken-3-ols. Treatment of the cis-halogenated olefins with dihydropyran in the presence of a catalytic amount of p-toluenesulfonic acid affords the tetrahydropyranyl ethers which are allowed to react with activated magnesium and cuprous iodide, thus yielding the desired 3-(tetrahydropyran-2-yl)oxy-cis-1-alkenyl copper compounds. For example, treatment of 1-octyne-3-ol according to the above reaction sequence yields 3-(tetrahydropyran-2-yl)oxy-cis-1-octenyl copper.

The 3-hydroxy-3-alkylated acetylenic compounds of this invention are prepared by employing the appropriately alkylated alkynyl boron, alkynyl gallium or alkynyl aluminum reactant. For example, treatment of methyl 3-hydroxy-5-oxocyclopent-1-eneheptanoate with tri(3methyl-3-[tetrahydropyran-2-yl]oxy-1-octynyl) aluminum, gallium or boron affords the epimeric methyl 3-hydroxy-2-(3-methyl-3-[tetrahydropyran-2-yl]oxy-1-octynyl)-5-oxocyclopentaneheptanoate. Typically, that compound may be hydrolyzed with a hydrolyzing agent such as hydrolytic acid, e.g. aqueous acetic acid, to yield the instant methyl 3-hydroxy-2-(3-hydroxy-3-methyl-1-octynyl)-5-oxocyclopentaneheptanoate.

Although the above description is concerned most particularly with the trialkynyl metallic compounds, is it understood that the lithium tetraalkynyl metallic salts and the dialkylalkynyl metallic compounds are equivalent and can be used in the same manner as described above to produce the instant compounds and to practice the instant process. The lithium tetraalkynyl metallic salts are prepared according to the same methods as the trialkynyl compounds except that the molar ratio of the appropriately substituted 1-alkyne and butyl lithium to the metallic halide is 4:1. For example, when 4 moles of butyl lithium and 4 moles of 3-(tetrahydropyran-2-yl)oxy-1-octyne is allowed to react with 1 mole of aluminum trichloride, there is afforded lithium tetra-(3-[tetrahydropyran-2-yl]oxy-1-octynyl) aluminate.

The dialkylalkynyl metallic reactants are prepared according to methods outlined for the preparation of the trialkynyl metallic reactants except that equimolar quantities of butyl lithium, the appropriate 1-alkyne and the dialkylated metallic halide are used. Typically, equimolar quantities of butyl lithium, 3-(tetrahydropyran-2-yl)oxy-1-octyne and dimethyl aluminum chloride are allowed to react to produce dimethyl [3-(tetrahydropyran-2-yl)oxy-1-octynyl] aluminum.

The organometallic reactants which are useful in the instant process preferably are employed in situ.

The epimeric mixtures produced by the methods outlined hereinbefore are separated by standard chromatographic methods. Thus, for example, the epimers of methyl 3-hydroxy-2-(1-octynyl)-5-oxocyclopentaneheptanoate are separated by column chromatography on silica gel with 5% ethyl acetate in benzene as eluent. Alternatively, the reactants may be optically resolved before they are alkenylated or alkynylated to produce the instant compounds.

It is understood that blocking groups other than the tetrahydropyranyl radical may be employed in the process. For example, (lower alkoxy)alkyl groups such as methoxymethyl and 1,1-dibutoxyethyl, and trialkylsilyl groups such as dimethyl-t-butylsilyl may be employed in place of the tetrahydropyranyl group. Generally, it is required that the blocking group be removable under conditions which will not destroy the hydroxyl substituent on the cyclopentane ring. However, when both the alicyclic and aliphatic hydroxyl groups are blocked with the same blocking group, both blocking groups may be removed under the same reaction conditions to afford the free hydroxy compound.

The instant process generally is carried out at a temperature between about −30°C. to 70°C., but not limited thereto. A temperature of between about 0° – 30° is preferred. The process generally is run in inert solvents such as ether, tetrahydrofuran and the like. Hydrolyzing agents employed in the instant process are illustrated by hydrolytic inorganic or organic acids, but not limited thereto. Aqueous acetic acid and methanolacetic acid mixtures are examples of hydrolytic acids encompassed above.

Reaction times for the instant process, though not critical, generally are held between about 2–24 hours but those times are not deemed limiting. During the course of the reaction it has been found desirable to agitate the reacting mixture. However, that step is merely preferable and is not deemed critical to the practice of the instant process.

The process of this invention is useful both for the production of racemic compounds and the optically active isomers. Thus, the optically active isomers of the reactants may first be obtained and then reacted to form optically active products. Alternatively, the compounds produced may be reacted as racemic compounds to produce the stereoisomeric products which then may be resolved by standard methods to afford the optically active products. Such resolution methods are well known in the art and are typified by elution chromatography, thin layer chromatography or standard chemical methods utilizing optically active amines and carboxylic acids.

Fully encompassed by this invention are the optical isomers of the instant stereoisomeric product mixtures. It is noted that the instant compounds possess 4-asymmetric carbon atoms. Thus, the asymmetry present at the 1-, 2- and 3-position of the cyclopentane ring and at the 3-position of the alkynyl side chain give rise to 16 possible optical isomers from each stereoisomeric mixture. Those optical isomers can be separated by methods well-known in the art as discussed hereinbefore.

The novel products of this invention are useful as pharmacological agents in view of their prostaglandin antagonist, anti-bacterial, anti-fungal and central nervous system-affective activity. The central nervous system-affective activity is demonstrated in the following assay based on that described by N. W. Dunham and P. S. Miya in *J. Amer. Pharm. Assoc.* (Sci. Ed.), 46, 208 (1957).

To each of ten male or female mice, weighing 20–30g., is administered, intragastrically, a dose of the compound to be tested. At a specific time after the administration of the test compound (2.5 hours), each mouse is placed on a rotating rod upon which untreated mice can remain indefinately. A dose of compound is rated active if ≥ 20% of the mice are unable to remain on the rod for 1 minute.

The anti-microbial activity is demonstrated by the ability of the compounds to inhibit the growth of bacteria such as *Erwinia sp.* and fungi such as *Trichophyton mentagrophytes* and *Verticillium albo-atrum*. Assays used to determine that activity are described in U.S. Pat. No. 3,631,186.

The compounds produced by the instant process also exhibit anti-ulcerogenic, prostaglandin antagonist, acetylchloine antagonist, and bradykinin antagonist activity when tested in the following assays.

The prostaglandin, acetylcholine and bradykinin antagonist activity is demonstrated in the following procedure which is substantially the same as that described by J. H. Sanner, *Arch. int. Pharmacodyn.*, 180 (1), 46 (1969):

Female albino guinea pigs weighing 200–500 g. are sacrificed by cervical dislocation and the ileum is quickly removed and placed in modified Tyrode solution containing ½ the usual amount of magnesium ions. Segments of ileum, about 2 centimeters long, are cut and mounted in a 2 or 4 ml. tissue bath containing the modified Tyrode solution. The solution is maintained at 37° and bubbled with a gaseous mixture of 95% oxygen and 5% carbon dioxide. Contractions are detected isotonically. Approximately equal submaximal contractions are obtained in preliminary trials by adjusting the doses of prostaglandin $E_2$(PGE$_2$), bradykinin, and acetylcholine added to the bath. Two control contractions are obtained at 3.5 minute intervals. A solution or suspension of the test compound in the bathing solution is then substituted for the original modified Tyrode solution. The test suspension is kept in constant contact with the tissue for the remainder of the experiment except for brief periods to drain the bath in preparation for rinsing with fresh test suspension. Three more contractions are elicited to each agonist in the presence of the test compound without interrupting the time sequence. The last two sets of treated responses are compared with the two sets of control responses. The first set of treated responses is not used for comparisons, being used only to maintain the timed sequence of injections during the period allowed for the tissue to become equilibrated with the antagonist. A compound is rated active if the mean of contractions produced by any agonist is reduced 75% or more by the test compound.

The anti-ulcerogenic activity of the compounds produced by the instant process is demonstrated in an assay described in U.S. Pat. No. 3,483,192.

The invention will appear more fully from the examples which follow. Those examples are given by way of illustration only and are not to be construed as limiting the invention either in spirit or in scope as many modifications both in materials and methods will be apparent to those skilled in the art. Temperatures are given in degrees Centigrade (°C.) and quantities of material in parts by weight unless parts by volume is specified. The relationship between parts by weight and parts by volume is the same as that existing between grams and milliliters. For the purposes of this invention, the term "racemic," when used in the examples in conjunction with a compound name for which the stereochemistry has been specified, indicates a racemic mixture of the compound named and its enantiomer.

EXAMPLE 1

To a stirred solution of 200 parts by volume of 1 M boronhydride in tetrahydrofuran at 0° under a nitrogen atmosphere is added, dropwise over a 30 minute period, 22 parts by catechol in 44 parts of tetrahydrofuran. That solution is stirred at room temperature for 1 hour. Then 16 parts of 1-hexyne is added and the solution is refluxed for 2 hours. The reaction mixture is cooled to 0° and treated with 54 parts of mercuric chloride. The resulting mixture is stirred at 0° for 1 hour and allowed to warm to room temperature. After standing at room temperature for 16 hours, the mixture is poured into a 3:1 water-acetone mixture and the white prepipitate which forms is collected and washed with water. Then the precipitate is dissolved in boiling hexane and the solution is filtered while hot and cooled to 0° to afford white crystals of trans-1-hexenyl mercuric chloride, melting at about 111°.

EXAMPLE 2

When an equivalent quantity of 1-octyne is substituted in the procedure of Example 1, there is produced trans-1-octenyl mercuric chloride, melting at about 104–105°.

EXAMPLE 3

To 1.0 part of 3(RS)-hydroxy-5-oxocyclopent-1-eneheptanoic acid dissolved in methanol is added dropwise a 5% ethereal diazomethane solution until a slight excess of diazomethane is present. That excess is detected when the solution exhibits a persistent yellow color. The solution then is evaporated to dryness under a nitrogen atmosphere to yield methyl 3(RS)-hydroxy-5-oxocyclopent-1-eneheptanoate.

EXAMPLE 4

A mixture consisting of 0.240 part of methyl 3(RS)-hydroxy-5-oxocyclopent-1-eneheptanoate, 0.200 part of 2(S)- aminoxyisocaproic acid and 4 parts of methanol is treated with 0.5 part of pyridine. That mixture is allowed to stand at room temperature for about 16 hours and then is poured into 45 parts of ethyl acetate and 20 parts by volume of 0.5 N hydrochloric acid. The ethyl acetate layer is separated, washed with water and dried over anhydrous sodium sulfate. The solvent is removed by evaporation under reduced pressure and the residue is chromatographed on silica gel using 1% ethyl acetate in chloroform as eluent to afford successive fractions of methyl 3(R)-hydroxy-5[(1-carboxyisoamyl)oxyimino]cyclopent-1-eneheptanoate, melting at about 62°–63° and methyl 3(S)-hydroxy-5-[(1-carboxyisoamyl)oxyimino]cyclopent-1-eneheptanoate.

Each of the above oximes is mixed with 1.5 parts of ammonium acetate, 1 part of acetic acid, 10 parts of water, 27 parts of tetrahydrofuran and 3.0 parts by volume of an aqueous 20% titanium trichloride solution and stirred at 60° for about 16 hours under a nitrogen atmosphere. Then each mixture is diluted with ether and water is added. The ether layer is separated and washed with an aqueous 2% sodium bicarbonate solution, water and dried over anhydrous sodium sulfate. The solvent is removed under reduced pressure to give, respectively, methyl 3(R)-hydroxy-5-oxocyclopent-1-eneheptanoate and methyl 3(S)-hydroxy-5-oxocyclopent-1-eneheptanoate.

EXAMPLE 5

A suspension of 1.6 parts of magnesium powder and 27 parts of tetrahydrofuran, distilled from an ethyl magnesium bromide solution, is treated with 1 part of mercuric chloride. After stirring the mixture for 15 minutes, 5.1 parts of trans-1-hexenyl mercuric chloride is added and that mixture is stirred for about 16 hours at room temperature. The supernatant is decanted from the excess magnesium and then stirred and cooled to −60° in an isopropanol/dry ice bath. Then 3.0 parts of cuprous iodide is added in one portion and the mixture is allowed to warm to −30°, at which temperature it is held for ten minutes. The mixture is cooled to −60° and 1.47 parts of tetrahydropyran-2-yl 5-oxocyclopent-1-eneheptanoate, dissolved in tetrahydrofuran, is added dropwise to the reaction mixture. That mixture is stirred for 30 minutes and then poured into a mixture consisting of 140 parts of ethyl ether and 100 parts by volume of aqueous 0.5 N hydrochloric acid. The ether layer is separated, washed with water and dried over anhydrous sodium sulfate. Then the solvent is removed under reduced pressure and the material remaining is dissolved in 40 parts of acetone containing 10 parts by volume of 1 N aqueous hydrochloric acid. That mixture is allowed to stand at room temperature for one hour and then it is diluted with water and extracted with ether. The ether extract is washed with water, dried over anhydrous sodium sulfate and stripped of solvent. The residue which remains is chromatographed on silica gel using ethyl acetate and benzene as eluent to give racemic 2β-(1-hexenyl)-5-oxo-1α-cyclopentaneheptanoic acid as a yellow oil. That compound displays absorption maxima in the infrared spectrum at about 1715 and 1739 reciprocal centimeters.

EXAMPLE 6

When an equivalent quantity of trans-1-octenyl mercuric chloride is substituted in the procedure of Example 5, there is produced racemic 2β-(1-octenyl)-5-oxo-1α-cyclopentaneheptanoic acid. That compound is recovered as a yellow oil and displays absorption in the infrared spectrum at about 1715 and 1739 reciprocal centimeters.

EXAMPLE 7

By substituting an equivalent quantity of methyl 3(RS)-hydroxy-5-oxocyclopent-1-eneheptanoate in the procedure of Example 5, there is produced racemic methyl 2β-(1-hexenyl)-3-hydroxy-5-oxo-1α-cyclopentaneheptanoate, racemic methyl 2α-(1-hexenyl)-3(R)-hydroxy-5-oxo-1β-cyclopentaneheptanoate and racemic methyl 2β-(1-hexenyl)-3(R)-hydroxy-5-oxo-1β-cyclopentaneheptanoate. Those compounds are recovered as yellow oils, and display an absorption maxima in the infrared spectrum at about 1744 reciprocal centimeters.

EXAMPLE 8

When equivalent quantities of trans-1-octenyl mercuric chloride and methyl 3(RS)-hydroxy-5-oxocyclopent-1-eneheptanoate are substituted in the procedure of Example 5, there is produced racemic methyl 2α-(1-octenyl)-3(R)-hydroxy-5-oxo-1β-cyclopentaneheptanoate, racemic methyl 2β-(1-octenyl)-3(R)-hydroxy-5-oxo-1α-cyclopentaneheptanoate and racemic methyl 2β-(1-octenyl)-3(R)-hydroxy-5-oxo-1β-cyclopentaneheptanoate. Those materials appear as yellow oils.

EXAMPLE 9

Equivalent quantities of methyl 3(RS)-(tetrahydropyran-2-yloxy)-5-oxocyclopent-1-eneheptanoate and trans-1-octenyl mercuric chloride and substituted in the procedure of Example 5. However, before chromatography, the tetrahydropyranyl ether is cleaved by dissolving the residue, which remains after stripping the solvent, in 5 parts by volume of a 19:10:6 acetic acid:-water:tetrahydrofuran mixture and warming to 60° for 10 minutes. Then the mixture is cooled and diluted with water and ether. The ethereal layer is separated and washed with water, dried over anhydrous sodium sulfate and stripped of solvent. Column chromatography on silica gel using ethyl acetate in benzene as eluent gives pure racemic methyl 2β-(1-octenyl)-3(R)-hydroxy-5-oxo-1α-cyclopentaneheptanoate as a yellow oil. That product is identical to the second product obtained in Example 8.

EXAMPLE 10

By substituting equivalent quantities of tetrahydropyran-2-yl 3(RS)-(tetrahydropyran-2-yloxy)-5-oxocyclopent-1-eneheptanoate and trans-1-octenyl mercuric chloride in the procedure of Example 5, and treating the residue as in Example 9 before chromatography, there is produced racemic 2β-(1-octenyl)-3(R)-hydroxy-5-oxo-1α-cyclopentaneheptanoic acid.

EXAMPLE 11

A solution of 0.800 part of 1-octyne in 7.1 parts of ethyl ether at −30° is treated with 2.6 parts by volume of a 2.28 M butyl lithium in hexane solution. That mixture is allowed to stir at room temperature for 1 hour and then it is cooled to −60°. 0.267 Part of aluminum trichloride is added and after stirring the solution for 2 hours at room temperature, 0.240 part of methyl 3-hydroxy-5-oxocyclopent-1-eneheptanoate dissolved in ether is added in one portion. That mixture is stirred at room temperature for 2 hours and then it is poured into a mixture of 70 parts of ethyl ether and 50 parts by volume of aqueous 0.5 N hydrochloric acid. The ether layer is separated, washed with water and dried over anhydrous sodium sulfate. After removal of the solvent, the remaining material is chromatographed on a silica gel column to give successively, upon elution with 5% ethyl acetate in benzene, racemic methyl 2α-(1-octynyl)-3(R)-hydroxy-5-oxo-1β-cyclopentaneheptanoate, melting at about 32°, and racemic methyl 2α-(1-octynyl)-3(R)-hydroxy-5-oxo-1α-cyclopentaneheptanoate, melting at about 41°–42°.

EXAMPLE 12

By substituting an equivalent quantity of 1-hexyne in the procedure of Example 11, there is produced racemic methyl 2α-(1-hexynyl)-3(R)-hydroxy-5-oxo-1β-cyclopentaneheptanoate and racemic methyl 2α-(1-hexynyl)-3(R)-hydroxy-5-oxo-1α-cyclopentaneheptanoate.

EXAMPLE 13

Substitution of an equivalent quantity of tetrahydropyran-2-yl 5-oxocyclopent-1-eneoctanoate in the procedure of Example 5 affords racemic 2β-(1-hexenyl)-5-oxo-1α-cyclopentaneoctanoic acid.

EXAMPLE 14

When an equivalent quantity of methyl 3(RS)-hydroxy-5-oxocyclopent-1-eneoctanoate is substituted in the procedure of Example 11, there is obtained racemic methyl 2α-(1-octynyl)-3(R)-hydroxy-5-oxo-1β-cyclopentaneoctanoate and racemic methyl 2α-(1-octynyl)-3(R)-hydroxy-5-cxo-1α-cyclopentaneoctanoate.

EXAMPLE 15

Substitution of an equivalent quantity of ethyl 3(RS)-hydroxy-5-oxocyclopent-1-eneheptanoate in the procedure of Example 11 yields racemic ethyl 2α-(1-octynyl)-3(R)-hydroxy-5-oxo-cyclopentaneheptanoate and racemic ethyl 2α-(1-octynyl)-3(R)-hydroxy-5-oxo-1α-cyclopentaneheptanoate.

EXAMPLE 16

A solution of 0.800 part of 1-octyne in 7.1 parts of ethyl ether, cooled to −60°, is treated with 2.6 parts by volume of 2.3 M butyl lithium in hexane solution and stirred at room temperature for 30 minutes. Then the reaction mixture is cooled to −60°, treated with 2.47 parts by volume of 0.81 M borontrichloride-toluene solution and stirred at −20° − −10° for 20 minutes. 0.240 Part of methyl 3(RS)-hydroxy-5-oxocyclopent-1-eneheptanoate, dissolved in ether, is added in one portion and the resulting mixture is stirred at −20° − −10° for 20 minutes. The reaction mixture is allowed to warm slowly to 0° and it is held at that temperature for 1 hour. Then it is poured into a mixture of 70 parts of ethyl ether and 50 parts by volume of aqueous 0.5 N hydrochloric acid. The ether layer is separated, washed with water and dried over anhydrous sodium sulfate. After the solvent is stripped, the material which remains is chromatographed on a silica gel column to give, upon elution with 5% ethyl acetate in benzene, racemic methyl 2α-(1-octynyl)-3(R)-hydroxy-5-oxo-1β-cyclopentaneheptanoate, racemic methyl 2β-(1-octynyl)-3(R)-hydroxy-5-oxo-1α-cyclopentaneheptanoate, racemic methyl 2β-(1-octynyl)-3(R)-hydroxy-5-oxo-1β-cyclopentaneheptanoate and racemic methyl 2α-(1-octynyl)-3(R)-hydroxy-5-oxo-1α-cyclopentaneheptanoate.

EXAMPLE 17

By substituting an equivalent quantity of methyl 3(RS)-acetoxy-5-oxocyclopent-1-eneheptanoate in the procedure of Example 5, there is afforded racemic methyl 3(R)-acetoxy-2β-(1-hexenyl)-5-oxo-1α-cyclopentaneheptanoate.

EXAMPLE 18

When an equivalent quantity of methyl 3(RS)-acetoxy-5-oxocyclopent-1-eneheptanoate is substituted in the procedure of Example 16, there is produced racemic methyl 2α-(1-octynyl)-3(R)-acetoxy-5-oxo-1β-cyclopentaneheptanoate, racemic methyl 2β-(1-octynyl)-3(R)-acetoxy-5-oxo-1α-cyclopentaneheptanoate, racemic methyl 2β-(1-octynyl)-3(R)-acetoxy-5-oxo-1β-cyclopentaneheptanoate and racemic methyl 2α-(1-octynyl)-3(R)-acetoxy-5-oxo-1α-cyclopentaneheptanoate.

EXAMPLE 19

Substitution of an equivalent quantity of ethyl 3(RS)-propionyloxy-5-oxocyclopent-1-eneheptanoate in the procedure of Example 16 affords racemic ethyl 2α-(1-octynyl)-3(R)-propionyloxy-5-oxo-1β-cyclopentaneheptanoate, racemic ethyl 2β-(1-octynyl)-3(R)-propionyloxy-5-oxo-1α-cyclopentaneheptanoate, cyclopentaneheptanoate, racemic ethyl 2β-(1-octynyl)-3(R)-propionyloxy-5-oxo-1β-cyclopentaneheptanoate and racemic ethyl 2α-(1-octynyl)-3(R)-propionyloxy-5-oxo-1α-cyclopentane=heptanoate.

EXAMPLE 20

By substituting an equivalent quantity of methyl 5-oxocyclopent-1-eneheptanoate in the procedure of Example 11 and otherwise following the procedure of Example 11, there is produced racemic methyl 2β-(1-octynyl)-5-oxo-1α-cyclopentaneheptanoate.

EXAMPLE 21

0.489 Part of cis-1-hexenyl bromide is dissolved in 5 parts of ether under a nitrogen atmosphere and then that solution is cooled to −10° and treated with 0.042 part of finely divided lithium. After the reaction is complete, the solution is cooled to −40° and 0.570 part of cuprous iodide is added. The solution is stirred for 10 minutes at −30° and then it is cooled to −60°. Then 0.294 part of tetrahydropyran-2-yl 5-oxocyclopent-1-eneheptanoate dissolved in ether is added dropwise and the reaction mixture is stirred for 30 minutes at −60°. The product is recovered in the same manner as described in Example 5 to yield racemic 2β-(1-hexenyl)-5-oxo-1α-cyclopentaneheptanoic acid.

EXAMPLE 22

Substitution of equivalent quantities of methyl 3(S)-hydroxy-5-oxocyclopent-1-eneheptanoate and methyl 3(R)-hydroxy-5-oxocyclopent-1-eneheptanoate in the procedure of Example 5 affords the corresponding optically active methyl 2-(1-hexenyl)-3-hydroxy-5-oxocyclopentaneheptanoates.

EXAMPLE 23

A solution of 1.47 parts of 3(RS)-(tetrahydropyran-2-yl)oxy-1-octyne in 7.1 parts of ether is treated at −40° with 2.6 parts by volume of a 2.3 M butyl lithium in hexane solution. The reaction mixture is stirred at room temperature for 1 hour, then cooled to −40°. 0.267 Part of aluminum trichloride is added and the mixture is stirred at room temperature for 2 hours. After that time, 0.240 part of methyl 3(RS)-hydroxy-5-oxocyclopent-1-eneheptanoate, dissolved in ether, is added and the resulting mixture is stirred at room temperature for about 16 hours. The reaction mixture then is poured into a mixture of 35.5 parts of ether and 20 parts by volume of an aqueous 0.5 N hydrochloric acid solution. The ethereal layer is separated, washed with water, dried over anhydrous sodium sulfate and stripped of solvent. The remaining material is chromatographed on silica gel with 20% ethyl acetate in benzene as eluent to yield, as a stereoisomeric mixture, methyl 3(RS)-hydroxy-2-(3(RS)-[tetrahydropyran-2-yl]oxy-1-octynyl)-5-oxocyclopentane-heptanoate.

That isomeric product is treated with a 19:10:6 mixture of acetic acid-water-tetrahydrofuran at 60° for 10 minutes. Then it is diluted with ether/benzene and the organic layer is separated, washed with water, dried over anhydrous sodium sulfate and chromatographed on silica gel. Elution with 30% ethyl acetate in benzene affords successively a mixture of racemic methyl 3(R)-hydroxy-2α-(3(R)-hydroxy-1-octynyl)-5-oxocyclopentane-1β-heptanoate and racemic methyl 3(R)-hydroxy-2α-(3(S)-hydroxy-1-octynyl)-5-oxocyclopentane-1β-heptanoate, as a yellow oil, displaying maxima in the nuclear magnetic resonance spectrum at 100 megaHertz in deuteriochloroform at about 64.40 and 63.63 and an infrared absorption maximum at 1748 reciprocal centimeters, and a mixture of racemic methyl 3(R)-hydroxy-2α-(3(R)-hydroxy-1-octynyl)-5-oxocyclopentane-1α-heptanoate and racemic methyl 3(R)-hydroxy-2α-(3(S)-hydroxy-1-octynyl)-5-oxocyclopentane-1α-heptanoate, which, when recrystallized from ether, melts at about 84°–85°. The latter mixture also exhibits maxima in the nuclear magnetic resonance spectrum at 100 megaHertz in deuteriochloroform at about 64.39 and 63.65. Those compounds are represented respectively, by the following structural formulas

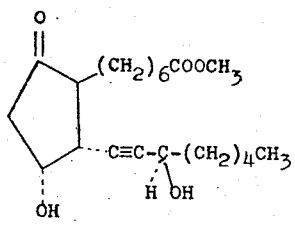 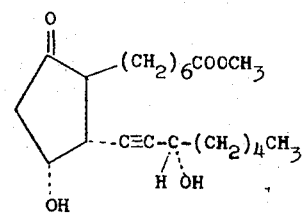

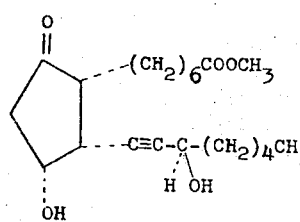 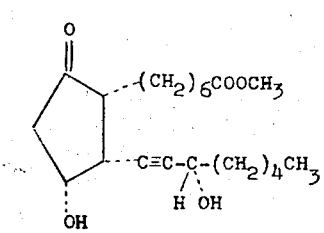

EXAMPLE 24

A solution of 1.47 parts of 3(RS)-tetrahydropyran-2-yl)oxy-1-octyne in 7.1 parts of ether is treated at −50° with 2.6 parts by volume of a 2.3 M butyl lithium in hexane solution. That mixture is stirred at room temperature for 1 hour and then cooled to −40°. 2.47 Parts by volume of a 0.81 M boron trichloride in toluene solution is added and the resulting solution is stirred at −30° − −20° for 30 minutes. After that time, an ethereal solution containing 0.240 part of methyl 3(RS)-hydroxy-5-oxocyclopent-1-eneheptanoate is added and the resulting reaction mixture is stirred at −20° for 1 hour at 0° for 2 hours and at room temperature for 2 hours. The crude reaction product is treated in the same manner as in Example 23, to yield after chromatography, elution being with 30% ethyl acetate in benzene, racemic methyl 3(R)-hydroxy-2α-(3(R)-hydroxy-1-octynyl)-5-oxocyclopentane-1β-heptanoate, racemic methyl 3(R)-hydroxy-2α-(3(S)-hydroxy-1octynyl)-5-oxocyclopentane-1β-heptanoate, racemic methyl 3(R)-hydroxy-2β-(3(R)-hydroxy-1-octynyl)-5-oxocyclopentane-1β-heptanoate, racemic methyl 3(R)-hydroxy-2β-(3(S)-hydroxy-1-octynyl)-5-oxocyclopentane-1β-heptanoate, racemic methyl 3(R)-hydroxy-2β-(3(R)-hydroxy-1-octynyl)-5-oxocyclopentane-1α-heptanoate, racemic methyl 3(R)-hydroxy-2β-(3(S)-hydroxy-1-octynyl)-5-oxocyclopentane-1α-heptanoate, racemic methyl 3(R)-hydroxy-2α-(3(R)-hydroxy-1-octynyl)-5-oxocyclopentane-1α-heptanoate, racemic methyl 3(R)-hydroxy-2α-(3(S)-hydroxy-1-octynyl)-5-oxocyclopentane-1α-heptanoate, racemic methyl 3(R)- hydroxy-1-octynyl)-5-oxocyclopentane-1α-heptanoate and racemic methyl 3(R)-hydroxy-2α-(3(S)-hydroxy-1octynyl)-5-oxocyclopentane-1α-heptanoate.

The first two compounds and the last two compounds are identical to those described in Example 23. The third and fourth compounds are recovered as a mixture displaying maxima in the nuclear magnetic resonance spectrum at 100 megaHertz in deuteriochloroform at about δ3.68 and δ4.56 and are represented by the following structural formulas and the fifth and sixth compounds are recovered as a mixture exhibiting peaks in the nuclear magnetic resonance spectrum at 100 megaHertz in deuteriochloroform at about δ4.40 and δ3.63, and are represented by the following structural formulas

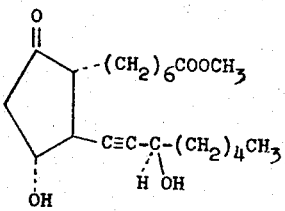
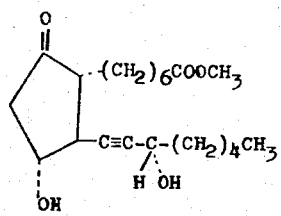

EXAMPLE 25

A mixture of 12.6 parts of 3(RS)1-octyn-3-ol and 9.2 parts of dihydropyran is treated with 0.100 part of p-toluenesulfonic acid, then allowed to stand at room temperature for 2 hours. After that time, the mixture is diluted with ether. The ethereal extract is washed successively with dilute sodium carbonate and water and dried over anhydrous sodium sulfate. The solvent is removed under reduced pressure to afford 3(RS)-(tetrahydropyran-2-yl)oxy-1-octyne.

A solution of 10.5 parts of the tetrahydropyranyl ether prepared above is dissolved in 16.5 parts of n-hexane and treated dropwise at −40° with 30 parts by volume of a diisobutyl aluminum hydride-hexane solution containing 0.19 part of diisobutyl aluminum hydride per milliliter of solution. The reaction mixture is allowed to warm to room temperature and is allowed to stand for 24 hours. Then the solution is warmed to 50° for 2 hours and stripped of solvent. The residue which remains is dissolved in 17.7 parts of tetrahydrofuran and treated at a temperature of −50° with a solution of 11.4 parts of iodine dissolved in 17.7 parts of tetrahydrofuran. After the addition is complete, the solution is allowed to warm to room temperature and is poured into a mixture consisting of ether and aqueous 0.5 N sulfuric acid. The ethereal extract is washed successively with water, sodium sulfite solution, sodium bicarbonate solution and water. Then it is dried over anhydrous sodium sulfate and the solvent is removed under reduced pressure. The material remaining is chromatographed on silica gel to afford trans-3(RS)-(tetrahydropyran-2-yl)oxy-1-iodo-1-octene. That material is characterized by a nuclear magnetic resonance spectrum with a doublet at δ5.95 (J = 14.5 cycles per second) and a doublet of triplets at δ6.5.

1.01 Parts of the above iodooctene compound is

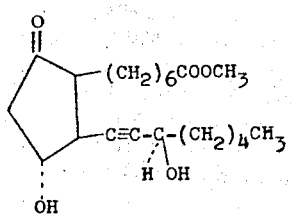
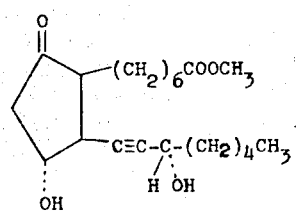

added in one portion to a mixture consisting of 0.300 part of magnesium powder suspended in 8.89 parts of tetrahydrofuran containing 0.100 part of mercuric chloride. That solution is stirred for 3–4 hours, then cooled to −60° and treated with 0.600 part of cuprous iodide. The solution is allowed to warm to −30°, then stirred for 10 minutes and cooled to −60°.

The above solution, containing 3(RS)-tetrahydropyran-2-yl)oxy-1-octenyl copper is treated dropwise with a tetrahydrofuran solution containing 0.324 part of methyl 3(RS)-(tetrahydropyran-2-yl)oxy-5-oxocyclopent-1-eneheptanoate. That mixture is stirred at −60° for 2 hours and then poured into a mixture of ether and 0.5 N aqueous hydrochloric acid. The ether layer is separated and washed with water, dried over anhydrous sodium sulfate and stripped of solvent. The residue which remains is taken up in 5 parts by volume of a mixture of acetic acid-water-tetrahydrofuran in a volumetric ratio of 19:10:6. Then it is warmed to 60°, held at that temperature for 10 minutes and diluted with ether and water. The ethereal layer is separated, washed with water, dried over anhydrous sodium sulfate and stripped of solvent. After chromatography on silica gel using 30% ethyl acetate in benzene as eluent, there is afforded racemic methyl 11(R),15(R)-dihydroxy-9-oxoprost-13-trans-enoate and racemic methyl 11(R),15(S)-dihydroxy-9-oxoprost-13-trans-enoate.

EXAMPLE 26

When an equivalent quantity of tetrahydropyran-2-yl 3(RS)-(tetrahydropyran-2-yl)oxy-5-oxocyclopent-1-eneheptanoate is substituted in the procedure of Example 25, there is afforded racemic 11(R),15(R)-dihydroxy-9-oxoprost-13-trans-enoic acid and racemic 11(R),15(S)-dihydroxy-9-oxoprost-13-trans-enoic acid.

EXAMPLE 27

Substitution of equivalent quantities of 3(R)-(tetrahydropyran-2-yl)oxy-1-octyne and methyl 3(R)-hydroxy-5-oxocyclopent-1-eneheptanoate in the procedure of Example 24 affords methyl 3(R)-hydroxy-2α-(3(R)-hydroxy-1-octynyl)-5-oxocyclopentane-1α-heptanoate, methyl 3(R)-hydroxy-2β-(3(R)-hydroxy-1-octynyl)-5-oxocyclopentane-1β-heptanoate, methyl 3(R)-hydroxy-2α-(3(R)-hydroxy-1-octynyl)-5-oxocyclopentane-1β-heptanoate and methyl 3(R)-hydroxy-2β-(3(R)-hydroxy-1-octynyl)-5-oxocyclopentane-1α-heptanoate.

EXAMPLE 28

By substituting equivalent quantities of 3(S)-tetrahydropyran-2-yl)oxy-1-octyne and methyl 3(R)-hydroxy-5-oxocyclopent-1-eneheptanoate in the procedure of Example 24, there is afforded methyl 3(R)-hydroxy-2α-(3(S)-hydroxy-1-octynyl)-5-oxocyclopentane-1α-heptanoate, methyl 3(R)-hydroxy-2β-(3(S)-hydroxy-1-octynyl)-5-oxocyclopentane-1β-heptanoate, methyl 3(R)-hydroxy-2α-(3(S)-hydroxy-1-octynyl)-5-oxocyclopentane-1β-heptanoate and methyl 3(R)-hydroxy-2β-(3(S)-hydroxy-1-octynyl)-5-oxocyclopentane-1α-heptanoate. Those compounds are represented respectively by the following structural formulas

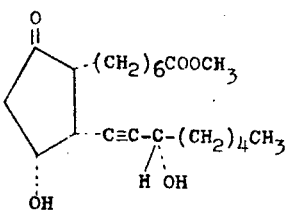
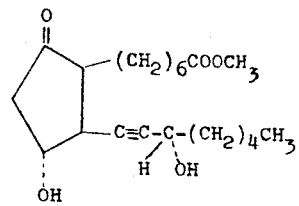
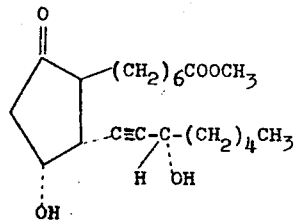
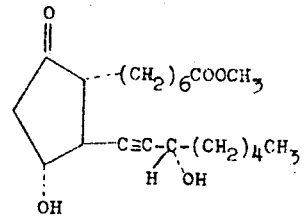

EXAMPLE 29

12.6 Parts of 3(RS) 1-octyne-3-ol is added dropwise to 100 parts by volume of a 1 N lithium aluminum hydride in tetrahydrofuran solution at −50°. The mixture is refluxed for 3 hours, then cooled and poured carefully into a mixture of ether and dilute hydrochloric acid. The ether layer is separated, washed with water, dried over anhydrous sodium sulfate and stripped of solvent. The 3(RS) 1-octen-3-ol which remains is characterized by a triplet centered at about δ5.2 and a multiplet centered at about δ5.95 in the nuclear magnetic resonance spectrum.

A mixture containing the 3(RS) 1-octen-3-ol produced above, 9.2 parts of dihydropyran and 0.100 part of p-toluenesulfonic acid is allowed to stand for 2 hours at room temperature. After that time the mixture is diluted with ether and the ether layer is separated, washed successively with dilute sodium carbonate solution and water, dried over anhydrous sodium sulfate and stripped of solvent to afford 3(RS)-(tetrahydropyran-2-yl)oxy-1-octene. 2.12 Parts of the tetrahydropyranyl ether so produced is dissolved in 15 parts by volume of chloroform and treated dropwise at 0° with a solution of 1.6 parts of bromine in 10 parts by volume of chloroform. After the addition is complete, the solution is washed with dilute sodium carbonate solution, then with water, and dried over anhydrous sodium sulfate. The solvent is removed under reduced pressure to yield 1,2-dibromo-3(RS)-(tetrahydropyran-2-yl)oxy-1-octane.

Method A 3.7 Parts of the dibromo compound is added to a solution containing 1.12 parts of potassium t-butoxide and 25 parts by volume of t-butanol. The reaction mixture is stirred at room temperature for 1 hour and then refluxed for 1 hour, cooled and then diluted with water. That mixture is extracted with ether and the ether extract is washed with water, dried over anhydrous sodium sulfate and stripped of solvent. The residue which remains is chromatographed on silica gel to give 1-bromo-3(RS)-(tetrahydropyran--yl)oxy-trans-1-octene. That material is employed in the same manner as in Example 25 to produce the organo-copper compound.

Method B

A mixture of 3.7 parts of 1,2-dibromo-3(RS)-(tetrahydropyran-2-yl)oxy-1-octene, 1.25 parts of 1,5-diazabicyclo[4.3.0]non-5-ene and 25 parts by volume of dimethyl sulfoxide is warmed at 80° for 1 hour, then cooled, diluted with water and extracted with ether. The ethereal extract is washed with water, dried over anhydrous sodium sulfate and stripped of solvent. The material which remains is chromatographed on silica gel to yield 1-bromo-3(RS)-(tetrahydropyran-2-yl)oxy-trans-1-octene, which is employed in the same manner as the iodooctene compound in Example 25 to produce the organo-copper compound, 3(RS)-(tetrahydropyran-2-yl)oxy-1-octenyl copper. That material is employed in situ as described in Example 25 to afford the products of Example 25.

EXAMPLE 30

100 Parts by volume of a 1 N lithium aluminum hydride in tetrahydrofuran solution, held at −50°, is treated dropwise with 12.6 parts of 3(RS) 1-octyn-3-ol. The mixture is refluxed for 3 hours, cooled again to −50° and treated dropwise with a solution of 50.8 parts of iodine in 100 parts by volume of tetrahydrofuran. After that addition is complete, the mixture is allowed to warm to room temperature and is poured into a mixture of ether and 1 N hydrochloric acid. Then the ether layer is separated, washed successively with water, sodium sulfite solution and water, dried over anhydrous sodium sulfate and stripped of solvent. The material which remains is distilled under reduced pressure to afford 1-iodo-3(RS)-hydroxy-cis-octene.

25.3 Parts of the above cis-iodo olefin and 9.2 parts of dihydropyran in 100 parts by volume of benzene is treated with 0.200 part of p-toluenesulfonic acid and the resulting mixture is allowed to stand at room temperature for about 16 hours. After that time, the solution is diluted with an aqueous 1% sodium carbonate solution and the organic and aqueous layers are separated. The organic layer is dried over anhydrous sodium sulfate and stripped of solvent to yield 1-iodo-3(RS)-(tetrahydropyran-2-yl)oxy-cis-octene.

EXAMPLE 31

A mixture of 12.6 parts of 3(RS) 1-octyn-3-octyn-3-ol, 9.2 parts of dihydropyran and 0.100 part of p-toluenesulfonic acid is allowed to stand for 2 hours at room temperature. Then the mixture is diluted with ether and the ethereal and aqueous layers are separated. The ether extract is washed with dilute aqueous sodium carbonate solution and water and dried over anhydrous sodium sulfate. After removal of solvent, there is afforded 3(RS)-(tetrahydropyran-2-yl)oxy-1-octyne.

EXAMPLE 32

When an equivalent quantity of 3(RS) 1-hexyn-3-ol is substituted in the procedure of Example 31, there is afforded 3(RS)-(tetrahydropyran-2-yl)oxy-1-hexyne.

EXAMPLE 33

By substituting an equivalent quantity of 3(S) 1-octyn-3-ol in the procedure of Example 31, there is obtained 3(S)-(tetrahydropyran-2-yl)oxy-1-octyne.

EXAMPLE 34

Substitution of an equivalent quantity of 3(RS) 1-hexyn-3-ol in the procedure of Example 25 affords a sterisomeric mixture of methyl 3-hydroxy-2-(3-hydroxy-1-hexenyl)-5-oxocyclopentaneheptanoate.

EXAMPLE 35

By substituting an equivalent quantity of 3(RS)-(tetrahydropyran-2-yl)oxy-1-hexyne in the procedure of Example 24, there is afforded a stereoisomeric mixture of methyl 3-hydroxy-2-(3-hydroxy-1-hexynyl)-5-oxocyclopentaneheptanoate.

EXAMPLE 36

Substitution of an equivalent quantity of methyl 3(RS)-hydroxy-5-oxocyclopent-1-eneoctanoate in the procedure of Example 24 affords methyl 3-hydroxy-2-(3-hydroxy-1-octynyl)-5-oxocyclopentaneoctanoate as a stereoisomeric mixture.

EXAMPLE 37

When an equivalent quantity of methyl 3(RS)-acetoxy-5-oxocyclopent-1-eneheptanoate is substituted in the procedure of Example 24, there is afforded a stereoisomeric mixture of methyl 3-acetoxy-2-(3-hydroxy-1-octynyl)-5-oxocyclopentaneheptanoate.

EXAMPLE 38

Substitution of an equivalent quantity of 3(RS) 3-hydroxy-3-methyl-1-octyne in the procedure of Example 31 yields 3(RS) 3-(tetrahydropyran-2-yl)oxy-3-methyl-1-octyne.

EXAMPLE 39

By substituting an equivalent quantity of 3(RS) 3-methyl-3-(tetrahydropyran-2-yl)oxy-1-octyne in the procedure of Example 24, there is afforded a stereoisomeric mixture of methyl 3-hydroxy-2-(3-hydroxy-3-methyl-1-octynyl)-5-oxocyclopentaneheptanoate.

EXAMPLE 40

A solution of 0.020 part of a mixture of racemic methyl 3(R)-hydroxy-2β-(3(R)-hydroxy-1-octynyl)-5-oxocyclopentane-1β-heptanoate and racemic methyl 3(R)-hydroxy-2β-(3(S)-hydroxy-1-octynyl)-5-oxocyclopentane-1β-heptanoate and 7.9 parts of ethanol is treated with 0.300 part of potassium acetate and refluxed for 1 hour. Then the mixture is diluted with water and extracted with ether. The ether layer is washed with water, dried over anhydrous sodium sulfate and evaporated under reduced pressure to afford crude product. Chromatography of that product on silica gel with ethyl acetate in benzene as eluent affords a mixture of racemic methyl 3(R)-hydroxy-2β-(3(R)-hydroxy-1-octynyl)-5-oxocyclopentane-1α-heptanoate and methyl 3(R)-hydroxy-2β-(3(S)-hydroxy-1-octynyl)-5-oxocyclopentane-1α-heptanoate.

EXAMPLE 41

By substituting equivalent quantities of 3(S)-(tetrahydropyran-2-yl)oxy-1-octyne and tetrahydropyran-2-yl 3(R)-(tetrahydropyran-2-yl)oxy-5-oxocyclopent-1-eneheptanoate in the procedure of Example 25, there is afforded (−)-PGE$_1$, (−)-11(R),15(S)-dihydroxy-9-oxoprost-13-trans-enoic acid.

EXAMPLE 42

Substitution of equivalent quantities of 3(R)-(tetrahydropyran-2-yl)oxy-1-octyne and tetrahydropyran-2-yl 3(S)-(tetrahydropyran-2-yl)oxy-5-oxocyclopent-1-eneheptanoate in the procedure of Example 25 affords (+)-PGE$_1$, (+)-11(S),15(R)-dihydroxy-9-oxo-8β,12α-prost-13-trans-enoic acid.

EXAMPLE 43

When equivalent quantities of 3(RS) 3-ethyl-3-(tetrahydropyran-2-yl)oxy-1-octyne and ethyl 3(RS)-hydroxy-5-oxocyclopent-1-eneheptanoate is substituted in the procedure of Example 24, there is obtained ethyl 3-hydroxy-2-(3-ethyl-3-hydroxy-1-octynyl)-5-oxocyclopentaneheptanoate as a stereoisomeric mixture.

EXAMPLE 44

A solution consisting of 1.47 parts of 3(RS)-(tetrahydropyran-2-yl)oxy-1-octyne and 7.1 parts of ether is treated at −40° with 3.48 parts by volume of a 2.3 M butyl lithium in hexane solution and stirred at room temperature for 1 hour. The solution is cooled to −40° and 0.267 part of aluminum trichloride is added. The resulting reaction mixture is stirred at room temperature for 2 hours to yield lithium tetra(3(RS)-[tetrahydropyran-2-yl]oxy-1-octynyl)aluminate, which is employed in situ in the manner described in EXample 23. Thus when 0.240 part of methyl 3(RS)-hydroxy-5-oxocyclopent-1-eneheptanoate is added to the above solution and processed according to the procedure outlined in Example 23, there are afforded products identical to those of Example 23.

EXAMPLE 45

By substituting an equivalent quantity of gallium trichloride in the procedure of Example 23, there are obtained products identical to those of Example 23.

EXAMPLE 46

Substitution of 0.572 part of dimethyl aluminum chloride in the procedure of Example 23 affords products identical to those obtained in Example 23.

EXAMPLE 47

When an equivalent quantity of 3(RS)-hydroxy-5-oxocyclopent-1-eneheptanoic acid is substituted in the procedure of Example 23, there is afforded racemic 3(R)-hydroxy-2α-(3(R)-hydroxy-1-octynyl)-5-oxocyclopentane-1β-heptanoic acid, racemic 3(R)-hydroxy-2α-(3(S)-hydroxy-1-octynyl)-5-oxocyclopentane-1β-heptanoic acid, racemic 3(R)-hydroxy-2α-(3(R)-hydroxy-1-octynyl)-5-oxocyclopentane-1α-heptanoic acid and racemic 3(R)-hydroxy-2α-(3(S)-hydroxy-1-octynyl)-5-oxocyclopentane-1α-heptanoic acid. Those compounds are represented, respectively, by the following structural formulas

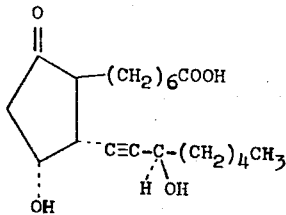
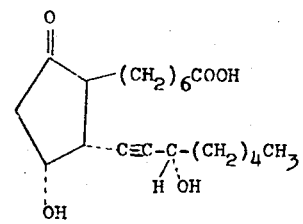

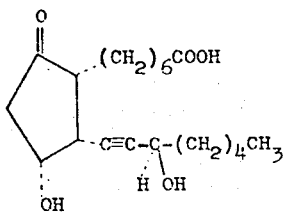
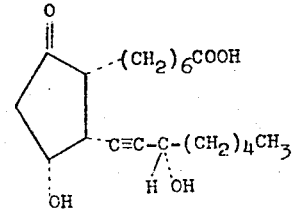

EXAMPLE 48

Substitution of an equivalent quantity of 3(RS)-hydroxy-5-oxocyclopent-1-eneheptanoic acid in the procedure of Example 24, affords, in addition to the compounds of Example 47, racemic 3(R)-hydroxy-2β-(3(R)-hydroxy-1-octynyl)-5-oxocyclopentane-1β-heptanoic acid, racemic 3(R)-hydroxy-2β-(3(S)-hydroxy-1-octynyl)-5-oxocyclopentane-1β-heptanoic acid, racemic 3(R)-hydroxy-2β-(3(R)-hydroxy-1-octynyl)-5-oxocyclopentane-1α-heptanoic acid and racemic 3(R)-hydroxy-2β-(3(S)-hydroxy-1-octynyl)-5-oxocyclopentane-1α-heptanoic acid. The latter compounds are represented structurally by the following formulas, respectively

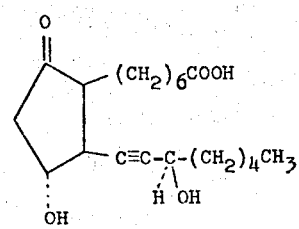

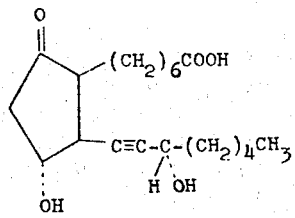

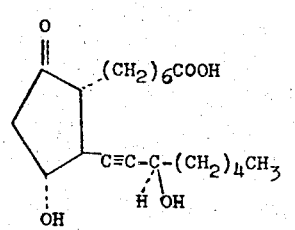

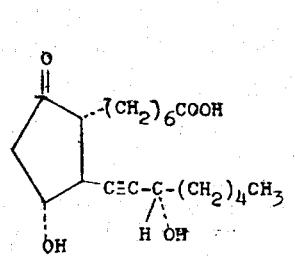

EXAMPLE 49

By substituting equivalent quantities of 3(S)-(tetrahydropyran-2-yl)oxy-1-octyne and 3(R)-hydroxy-5-oxocyclopent-1-eneheptanoic acid in the procedure of Example 24, there is obtained 3(R)-hydroxy-2α-(3(S)-hydroxy-1-octynyl)-5-oxocyclopentane-1α-heptanoic acid, 3(R)-hydroxy-2β-(3(S)-hydroxy-1-octynyl)-5oxocyclopentane-1β-heptanoic acid, 3(R)-hydroxy-2α-(3(S)-hydroxy-1-octynyl)-5-oxocyclopentane-1β-heptanoic acid and 3(R)-hydroxy-2β-(3(S)-hydroxy-1-octynyl)-5-oxocyclopentane-1α-heptanoic acid. Those compounds are respectively represented by the following formulas

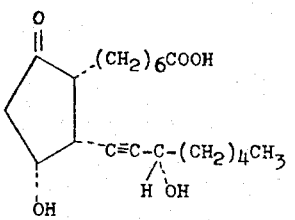

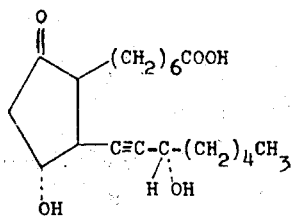

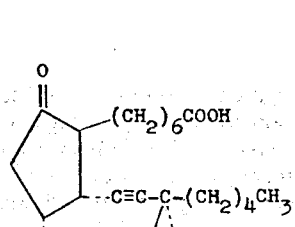

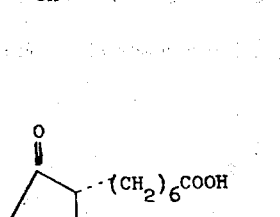

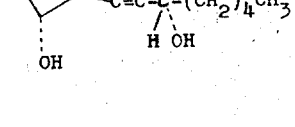

EXAMPLE 50

A solution of 1.28 parts of trans 1-octenyl mercuric chloride dissolved in 8.9 parts of tetrahydrofuran is treated under an argon atmosphere with 0.100 part of lithium wire. The mixture is stirred under argon for about 16 hours and then the liquid is decanted under a nitrogen atmosphere from the excess lithium which remains. The decanted liquid is cooled to −40° and 0.380 part of cuprous iodide is added. After stirring the mixture at −30° for 10 minutes, a tetrahydrofuran solution containing 0.320 part of methyl 3(RS)-(tetrahydropyran-2-yl)oxy-5-oxocyclopent-1-eneheptanoate is added dropwise. When the addition is complete, the solution is stirred at −30° for 30 minutes and poured into a mixture of ether and aqueous 0.5 N hydrochloric acid. The ethereal layer is separated, washed with water and dried over anhydrous sodium sulfate. Solvent is removed by evaporation under reduced pressure and the remaining material is dissolved in a 19:10:6 mixture of acetic acid-water-tetrahydrofuran. That solution is warmed to 60° and held at that temperature for 10 minutes, then diluted with ether/benzene. The organic layer is separated, washed with water and dried over anhydrous sodium sulfate. After the solvent is removed under reduced pressure, the material which remains is chromatographed on a silica gel column. Elution with ethyl acetate in benzene affords a racemic mixture of methyl 3(R)-hydroxy-2β-(trans-1-octenyl)-5-oxocyclopentane-1α-heptanoate and methyl 3(S)-hydroxy-2α-(trans-1-octenyl)-5-oxocyclopent-1β-heptanoate.

What is claimed is:
1. A compound of the formula

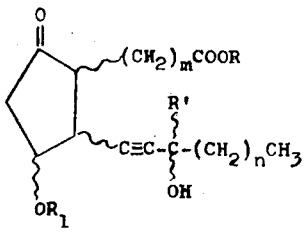

wherein R is hydrogen or a lower alkyl radical containing 1 to 7 carbon atoms, R' is hydrogen or a lower alkyl radical containing 1 to 4 carbon atoms, $R_1$ is hydrogen or a lower alkanoyl radical containing 1 to 7 carbon atoms, m is an integer greater than 5 and less than 8, n is an integer greater than 1 and less than 6 and the wavy lines represent the α or β configuration or the epimeric mixture.

2. As in claim 1, a compound of the formula

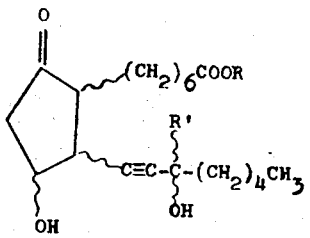

wherein R is hydrogen or a lower alkyl radical containing 1 to 7 carbon atoms, R' is hydrogen or a lower alkyl radical containing 1 to 4 carbon atoms, and the wavy lines represent the α or β configuration or the epimeric mixture.

3. As in claim 1, a compound of the formula

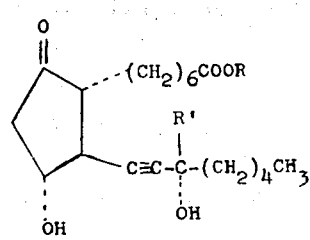

wherein R is hydrogen or a lower alkyl radical containing 1 to 7 carbon atoms, and R' is hydrogen or a methyl radical.

4. As in claim 1, the compound which is a mixture of racemic methyl 3(R)-hydroxy-2α-(3(R)-hydroxy-1-octynyl)-5-oxocyclopentane-1β-heptanoate and racemic methyl 3(R)-hydroxy-2α-(3(S)-hydroxy-1-octynyl)-5-oxocyclopentane-1β-heptanoate.

5. As in claim 1, the compound which is a mixture of racemic methyl 3(R)-hydroxy-2α-(3(R)-hydroxy-1-octynyl)-5-oxocyclopentane-1α-heptanoate and racemic methyl 3(R)-hydroxy-2α-(3(S)-hydroxy-1-octynyl)-5-oxocyclopentane-1α-heptanoate.

6. As in claim 1, the compound which is a mixture of racemic methyl 3(R)-hydroxy-2α-(3(R)-hydroxy-3(S)-methyl-1-octynyl)-5-oxocyclopentane-1β-heptanoate and racemic methyl 3(R)-hydroxy-2α-(3(S)-hydroxy-3(R)-methyl-1-octynyl)-5-oxocyclopentane-1β-heptanoate.

7. As in Claim 1, the compound which is a mixture of racemic methyl 3(R)-hydroxy-2α-(3(R)-hydroxy-3(S)-methyl-1-octynyl)-5-oxocyclopentane-1α-heptanoate and racemic methyl 3(R)-hydroxy-2α-(3(S)-hydroxy-3(R)-methyl-1-octynyl)-5-oxocyclopentane-1α-heptanoate.

8. As in claim 1, the compound which is a racemic mixture of methyl 11(R),15(S)-dihydroxy-9-oxoprost-13-ynoate and methyl 11(S),15(R)-dihydroxy-9-oxo-8β,12α-prost-13-ynoate.

9. As in claim 1, the compound which is a racemic mixture of 11(R),15(S)-dihydroxy-9-oxoprost-13-ynoic acid and 11(S),15(R)-dihydroxy-9-oxo-8β,12α-prost-13-ynoic acid.

* * * * *